(12) United States Patent
Lochead et al.

(10) Patent No.: US 7,211,581 B2
(45) Date of Patent: May 1, 2007

(54) SUBSTITUTED 2-(DIAZA-BICYCLO-ALKYL)-PYRIMIDONE DERIVATIVES

(75) Inventors: Alistair Lochead, Charenton le Pont (FR); Mourad Saady, Paris (FR); Franck Slowinski, Thieux (FR); Philippe Yaiche, Les Lilas (FR)

(73) Assignees: Sanofi-Aventis, Paris (FR); Mitsubishi Pharma Corporation, Tokyo (JP)

( * ) Notice: Subject to any disclaimer, the term of this patent is extended or adjusted under 35 U.S.C. 154(b) by 0 days.

(21) Appl. No.: 11/219,923

(22) Filed: Sep. 6, 2005

(65) Prior Publication Data

US 2006/0025417 A1 Feb. 2, 2006

Related U.S. Application Data

(63) Continuation of application No. PCT/EP2004/003050, filed on Mar. 5, 2004.

(30) Foreign Application Priority Data

| Mar. 7, 2003 | (EP) | ................... | 03290570 |
| Mar. 7, 2003 | (EP) | ................... | 03290571 |

(51) Int. Cl.
| C07D 401/14 | (2006.01) |
| C07D 403/14 | (2006.01) |
| A61K 31/506 | (2006.01) |
| A61K 31/444 | (2006.01) |
| A61P 3/10 | (2006.01) |

(52) U.S. Cl. ...................... 514/273; 544/320
(58) Field of Classification Search ................ 544/320; 514/273
See application file for complete search history.

(56) References Cited

FOREIGN PATENT DOCUMENTS

| EP | 0400661 | 12/1990 |
| EP | 0841326 | 5/1998 |
| EP | 1136483 | 9/2001 |
| WO | WO 03/072579 | 9/2003 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition, vol. 1, 1004-1010, 1996.*
Jope et al., Trends in Biochemical Sciences, 20(2): 95-102, 2004.*
Cohen et al., Nature Reviews/Molecular Biology 2: 769-776, 2001.*

* cited by examiner

*Primary Examiner*—Venkataraman Balasubramanian
(74) *Attorney, Agent, or Firm*—Balaram Gupta

(57) ABSTRACT

The invention relates to a 2-(diaza-bicyclo-alkyl)-pyrimidone derivative represented by formula (I):

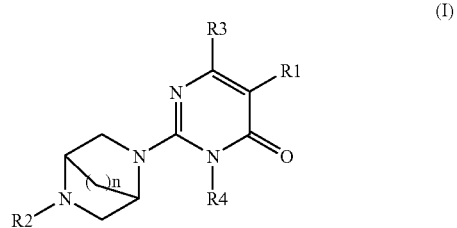

wherein:
R1 represents a hydrogen atom, a $C_{1-6}$ alkyl group or a halogen atom; R2 represents a hydrogen atom, a $C_{1-6}$ alkyl group optionally substituted by 1 to 4 substituents selected from a halogen atom, a hydroxyl group, a $C_{1-4}$ alkoxy group; a $C_{1-2}$ perhalogenated alkyl group, a benzyl group, a phenethyl group, a benzyloxycarbonyl group, a $C_{1-4}$ alkoxy carbonyl group, a benzene ring, a naphthalene ring, a quinoline ring, a phthalazine ring, a 5,6,7,8-tetrahydronaphthalene ring, a pyridine ring, an indole ring, a pyrrole ring, a thiophene ring, a benzenesulfonyl group, a benzoyl group, a pyridazine ring, a furan ring and an imidazole ring; each of the benzyl group, the phenethyl group, the benzyloxycarbonyl group, the benzenesulfonyl group, the benzoyl group and the benzene, naphthalene, quinoline, phthalazine, 5,6,7,8-tetrahydronaphthalene, pyridine, indole, pyrrole and thiophene rings being optionally substituted by 1 to 4 substituents selected from a $C_{1-6}$ alkyl group, a benzene ring, a halogen atom, a $C_{1-2}$ perhalogenated alkyl group, a $C_{1-3}$ halogenated alkyl group, a hydroxyl group, a $C_{1-4}$ alkoxy group, a nitro group, a cyano group, an amino group, a $C_{1-6}$ monoalkylamino group and a $C_{2-10}$ dialkylamino group; R3 represents a 2, 4 or 5-pyrimidine ring or a 2, 3 or 4-pyridine ring, the rings being optionally substituted by a $C_{1-4}$ alkyl group, $C_{1-4}$ alkoxy group or a halogen atom; R4 represents a $C_{1-4}$ alkyl group optionally substituted by a hydroxyl group, a $C_{1-4}$ alkoxy group or a halogen atom and n represents 1 or 2; or a salt thereof, or a solvate thereof or a hydrate thereof. The invention relates also to a medicament comprising the said derivative or a salt thereof as an active ingredient which is used for preventive and/or therapeutic treatment of a neurodegenerative disease caused by abnormal activity of GSK3β, such as Alzheimer's disease.

7 Claims, No Drawings

SUBSTITUTED 2-(DIAZA-BICYCLO-ALKYL)-PYRIMIDONE DERIVATIVES

CROSS-REFERENCE

This application is a continuation of WO International Application No. PCT/EP 2004/003050, filed 5 Mar. 2004, which WO application claims the benefit of priority of EP Applications Nos. 03290570.5 and 03290571.3, both filed on 7 Mar. 2003.

FIELD OF THE INVENTION

The present invention relates to compounds that are useful as an active ingredient of a medicament for preventive and/or therapeutic treatment of neurodegenerative diseases caused by abnormal activity of GSK3β.

BACKGROUND OF THE INVENTION

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several taupathies. Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as P53 and Bax. Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases. These include, in a non-limiting manner, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

In addition GSK3β may find application in the treatment of other diseases such as: Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as P53 and Bax. Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

SUMMARY OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that Gr compounds represented by the following formula (I) had the desired activity and were useful as an active ingredient of a medicament for preventive and/or therapeutic treatment of the aforementioned diseases.

DETAILED DESCRIPTION OF THE INVENTION

The present invention thus provides novel compounds, including the salts, solvates or hydrates thereof that are 2-(diaza-bicyclo-alkyl)-pyrimidone derivatives represented by formula (I):

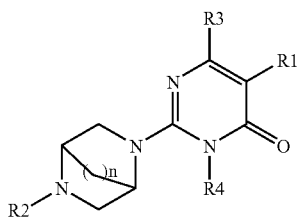

(I)

wherein:

R1 represents a hydrogen atom, a $C_{1-6}$ alkyl group or a halogen atom;

R2 represents a hydrogen atom, a $C_{1-6}$ alkyl group optionally substituted by 1 to 4 substituents selected from a halogen atom, a hydroxyl group, a $C_{1-4}$ alkoxy group; a $C_{1-2}$ perhalogenated alkyl group, a benzyl group, a phenethyl group, a benzyloxycarbonyl group, a $C_{1-4}$ alkoxy carbonyl group, a benzene ring, a naphthalene ring, a quinoline ring, a phthalazine ring, a 5,6,7,8-tetrahydronaphthalene ring, a pyridine ring, an indole ring, a pyrrole ring, a thiophene ring, a benzenesulfonyl group, a benzoyl group, a pyridazine ring, a furan ring and an imidazole ring; each of the benzyl group, the phenethyl group, the benzyloxycarbonyl group, the benzenesulfonyl group, the benzoyl group and the benzene, naphthalene, quinoline, phthalazine, 5,6,7,8-tetrehydronaphthalene, pyridine, indole, pyrrole and thiophene rings being optionally substituted by 1 to 4 substituents selected from a $C_{1-6}$ alkyl group, a benzene ring, a halogen atom, a $C_{1-2}$ perhalogenated alkyl group, a $C_{1-3}$ halogenated alkyl group, a hydroxyl group, a $C_{1-4}$ alkoxy group, a nitro group, a cyano group, an amino group, a $C_{1-6}$ monoalkylamino group and a $C_{2-10}$ dialkylamino group;

R3 represents a 2, 4 or 5-pyrimidine ring or a 2, 3 or 4-pyridine ring, the rings being optionally substituted by a $C_{1-4}$ alkyl group, $C_{1-4}$ alkoxy group or a halogen atom;

R4 represents a $C_{1-4}$ alkyl group optionally substituted by a hydroxyl group, a $C_{1-4}$ alkoxy group or a halogen atom; and n represents 1 or 2; or a salt thereof, or a solvate thereof or a hydrate thereof.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as: Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

As further preferred embodiments of the present invention, there are provided the aforementioned medicament wherein the diseases are neurodegenerative diseases and are selected from the group consisting of Alzheimer's disease, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma, and the aforementioned medicament in the form of pharmaceutical composition containing the above substance as an active ingredient together with one or more pharmaceutical additives.

The present invention further provides an inhibitor of GSK3β activity comprising as an active ingredient a substance selected from the group consisting of the 2-(diaza-bicyclo-alkyl)-pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of the 2-(diaza-bicyclo-alkyl)-pyrimidone derivatives of formula (I) and the physiologically acceptable salts thereof, and the solvates thereof and the hydrates thereof; and a use of a substance selected from the group consisting of the 2-(diaza-bicyclo-alkyl)-pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The $C_{1-4}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl group represents an alkyl group wherein all the hydrogen have been substituted by a halogeno, for example a $CF_3$ or $C_2F_5$;

The $C_{1-3}$ halogenated alkyl group represents an alkyl group wherein at least one hydrogen has not been substituted by an halogen atom;

The $C_{1-6}$ monoalkylamino group represents an amino group substituted by one $C_{1-6}$ alkyl group, for example, methylamino group, ethylamino group, propylamino group, isopropylamino group, butylamino group, isobutylamino group, tert-butylamino group, pentylamino group and isopentylamino group;

The $C_{2-10}$ dialkylamino group represents an amino group substituted by two $C_{1-5}$ alkyl groups, for example, dimethylamino group, ethylmethylamino group, diethylamino group, methylpropylamino group and diisopropylamino group;

The leaving group represents a group which could be easily cleaved and substituted, such a group may be for example a tosyl, a mesyl, a bromide and the like.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the 2-(diaza-bicyclo-alkyl)-pyrimidone derivatives represented by the aforementioned formula (I) and salts thereof, their solvates and hydrates also fall within the scope of the present invention. The 2-(diaza-bicyclo-alkyl)-pyrimidone derivatives represented by the aforementioned formula (I) may have one or more asymmetric carbon atoms. As for the stereochemistry of such asymmetric carbon atoms, they may independently be in either (R) and (S) configuration, and the derivative may exist as stereoisomers such as optical isomers, or diastereoisomers. Any stereoisomers in pure form, any mixtures of stereoisomers, racemates and the like fall within the scope of the present invention.

Examples of compounds of the present invention are shown in table 1 hereinafter. However, the scope of the present invention is not limited by these compounds.

One of the embodiments of the present invention represented by formula (I) include also: Compounds wherein R3 represents a 4- or 5-pyrimidine ring and more preferably 4-pyrimidine ring or R3 represents a 3- or 4-pyridine ring and more preferably a 4-pyridine ring, the rings being optionally substituted by a $C_{1-2}$ alkyl group, a $C_{1-2}$ alkoxy group or a halogen atom.

Another embodiment of the present invention include compounds represented by formula (I) as follows:
(1) Compounds wherein R1 represents a hydrogen atom, a $C_{1-3}$ alkyl group or a halogen atom; more preferably a hydrogen atom; and/or
(2) Compounds wherein when R3 represents a pyrimidine ring optionally substituted, R2 represents a hydrogen atom, a benzyl group, a phenethyl group, a benzyloxycarbonyl group, a $C_{1-4}$ alkoxy carbonyl group, a benzene ring, a quinoline ring, a phthalazine ring, a pyridine ring, a benzenesulfonyl group, a benzoyl group or a pyridazine ring; the benzyl group, the phenethyl group, the benzyloxycarbonyl group, the benzenesulfonyl group, the benzoyl group and the rings being optionally substituted by 1 to 4 substituents; or when R3 represents a pyridine ring optionally substituted, R2 represents a hydrogen atom, a $C_{1-4}$ alkoxy carbonyl group, a pyridine ring, a benzene ring, a naphthalene ring, a benzyl group, a benzoyl group; the groups or the rings being optionally substituted; and/or
(3) Compounds wherein R3 represents an unsubstituted 4-pyrimidine ring; and/or
(4) R4 represents a $C_{1-2}$ alkyl group preferably a methyl.

Particularly compounds of the present invention represented by formula (I), wherein R3 is a pyrimidine ring, include compounds:
1: (1S)-1-Methyl-2-[5-(5-phenyl-pyridin-3-yl)-2,5-diaza-bicyclo[2.2.1]hept-2-yl]-1H-[4,4']bipyrimidinyl-6-one,
2: (1S)-1-Methyl-2-(5-pyridin-3-yl-2,5-diaza-bicyclo[2.2.1]hept-2-yl)-1H-[4,4']bipyrimidinyl-6-one,
3: (1S)-1-Methyl-2-(5-quinolin-3-yl-2,5-diaza-bicyclo[2.2.1]hept-2-yl)-1H-[4,4']bipyrimidinyl-6-one,
4: (1R)-1-Methyl-2-(5-pyridin-3-yl-2,5-diaza-bicyclo[2.2.1]hept-2-yl)-1H-[4,4']bipyrimidinyl-6-one,
5: (1S)-2-[5-(4-Fluoro-phenyl)-2,5-diaza-bicyclo[2.2.1]hept-2-yl]-1-methyl-1H-[4,4']bipyrimidinyl-6-one,
6: (1R)-2-[5-(6-Chloro-quinolin-3-yl)-2,5-diaza-bicyclo[2.2.1]hept-2-yl]-1-methyl-1H-[4,4']bipyrimidinyl-6-one,
7: (1S)-5-(1-Methyl-6-oxo-1,6-dihydro-[4,4']bipyrimidinyl-2-yl)-2,5-diaza-bicyclo[2.2.1]heptane-2-carboxylic acid tert-butyl ester,
8: (1S)-2-[5-(6-Bromo-pyridin-3-yl)-2,5-diaza-bicyclo[2.2.1]hept-2-yl]-1-methyl-1H-[4,4']bipyrimidinyl-6-one,
9 (1S)-2-[5-(6-Chloro-pyridazin-3-yl)-2,5-diaza-bicyclo[2.2.1]hept-2-yl]-1-methyl-1H-[4,4']bipyrimidinyl-6-one,
10 (1S)-2-[5-(5-Bromo-pyridin-2-yl)-2,5-diaza-bicyclo[2.2.1]hept-2-yl]-1-methyl-1H-[4,4']bipyrimidinyl-6-one,
11: (1S)-2-[5-(4-Chloro-phthalazin-1-yl)-2,5-diaza-bicyclo[2.2.1]hept-2-yl]-1-methyl-1H-[4,4']bipyrimidinyl-6-one,
12: (1S)-2-[5-(4-Chloro-phenyl)-2,5-diaza-bicyclo[2.2.1]hept-2-yl]-1-methyl-1H-[4,4']bipyrimidinyl-6-one,
13: (1S)-2-[5-(3-Fluoro-phenyl)-2,5-diaza-bicyclo[2.2.1]hept-2-yl]-1-methyl-1H-[4,4']bipyrimidinyl-6-one,
14: (1S)-2-(2,5-Diaza-bicyclo[2.2.1]hept-2-yl)-1-methyl-1H-[4,4']bipyrimidinyl-6-one,
15: (1S)-1-Methyl-2-(5-p-tolyl-2,5-diaza-bicyclo[2.2.1]hept-2-yl)-1H-[4,4']bipyrimidinyl-6-one,
16: (1S)-2-(5-Benzoyl-2,5-diaza-bicyclo[2.2.1]hept-2-yl)-1-methyl-1H-[4,4']bipyrimidinyl-6-one,
17 (1S)-1-Methyl-2-[5-(toluene-4-sulfonyl)-2,5-diaza-bicyclo[2.2.1]hept-2-yl]-1H-[4,4']bipyrimidinyl-6-one,
18: (1S)-5-(1-Methyl-6-oxo-1,6-dihydro-[4,4']bipyrimidinyl-2-yl)-2,5-diaza-bicyclo[2.2.1]heptane-2-carboxylic acid benzyl ester
19: (1S)-1-Methyl-2-(5-phenethyl-2,5-diaza-bicyclo[2.2.1]hept-2-yl)-1H-[4,4']bipyrimidinyl-6-one,
20: (1S)-2-(5-Benzyl-2,5-diaza-bicyclo[2.2.1]hept-2-yl)-1-methyl-1H-[4,4']bipyrimidinyl-6-one,
21: (1S)-2-[5-(2(S)-Hydroxy-2-phenyl-ethyl)-2,5-diaza-bicyclo[2.2.1]hept-2-yl]-1-methyl-1H-[4,4']bipyrimidinyl-6-one,
22: (1S)-1-Methyl-2-(5-pyridin-2-yl-2,5-diaza-bicyclo[2.2.1]hept-2-yl)-1H-[4,4']bipyrimidinyl-6-one,
23: (1S)-1-Methyl-2-(5-pyridin-4-yl-2,5-diaza-bicyclo[2.2.1]hept-2-yl)-1H-[4,4']bipyrimidinyl-6-one,
24: (1S)-2-(5-(4-Bromo-benzoyl)-2,5-diaza-bicyclo[2.2.1]hept-2-yl)-1-methyl-1H-[4,4']bipyrimidinyl-6-one, 25 (1S)-2-(5-(4-Chloro-benzoyl)-2,5-diaza-bicyclo[2.2.1]hept-2-yl)-1-methyl-1H-[4,4']bipyrimidinyl-6-one,
26: (1S)-2-(5-(4-Fluoro-benzoyl)-2,5-diaza-bicyclo[2.2.1]hept-2-yl)-1-methyl-1H-[4,4']bipyrimidinyl-6-one,
27: (1S)-2-(5-(4-Methoxy-benzoyl)-2,5-diaza-bicyclo[2.2.1]hept-2-yl)-1-methyl-1H-[4,4']bipyrimidinyl-6-one,
28: (1S)-2-(5-(4-Methyl-benzoyl)-2,5-diaza-bicyclo[2.2.1]hept-2-yl)-1-methyl-1H-[4,4']bipyrimidinyl-6-one,
29: (1S)-2-(5-(4-Phenyl-benzoyl)-2,5-diaza-bicyclo[2.2.1]hept-2-yl)-1-methyl-1H-[4,4']bipyrimidinyl-6-one,
30: (1S)-2-(5-(4-Trifluoromethyl-benzoyl)-2,5-diaza-bicyclo[2.2.1]hept-2-yl)-1-methyl-1H-[4,4']bipyrimidinyl-6-one,
31: (1S)-2-(5-(3-Methyl-benzoyl)-2,5-diaza-bicyclo[2.2.1]hept-2-yl)-1-methyl-1H-[4,4']bipyrimidinyl-6-one,
32: (1S)-2-(5-(3-Methoxy-benzoyl)-2,5-diaza-bicyclo[2.2.1]hept-2-yl)-1-methyl-1H-[4,4']bipyrimidinyl-6-one,
33: (1S)-2-(5-(3-Fluoro-benzoyl)-2,5-diaza-bicyclo[2.2.1]hept-2-yl)-1-methyl-1H-[4,4']bipyrimidinyl-6-one,
34: (1S)-2-(5-(3-Bromo-benzoyl)-2,5-diaza-bicyclo[2.2.1]hept-2-yl)-1-methyl-1H-[4,4']bipyrimidinyl-6-one,
35: (1S)-2-(5-(3-Cyano-benzoyl)-2,5-diaza-bicyclo[2.2.1]hept-2-yl)-1-methyl-1H-[4,4']bipyrimidinyl-6-one,
36: (1S)-2-(5-(3-Chloro-benzoyl)-2,5-diaza-bicyclo[2.2.1]hept-2-yl)-1-methyl-1H-[4,4']bipyrimidinyl-6-one; and compounds of the present invention represented by formula (I) wherein R3 is a pyridine ring:
1': (1S)-5-(1-Methyl-6-oxo-4-pyridin-4-yl-1,6-dihydro-pyrimidin-2-yl)-2,5-diaza-bicyclo[2.2.1]heptane-2-carboxylic acid tert-butyl ester
2': (1S)-2-(2,5-Diaza-bicyclo[2.2.1]hept-2-yl)-3-methyl-6-pyridin-4-yl-3H-pyrimidin-4-one,
3': (1S)-2-[5-(4-Chloro-phenyl)-2,5-diaza-bicyclo[2.2.1]hept-2-yl]-3-methyl-6-pyridin-4-yl-3H-pyrimidin-4-one,
4': (1S)-3-Methyl-6-pyridin-4-yl-2-(5-p-tolyl-2,5-diaza-bicyclo[2.2.1]hept-2-yl)-3H-pyrimidin-4-one,
5': (1S)-2-[5-(4-Bromo-benzoyl)-2,5-diaza-bicyclo[2.2.1]hept-2-yl]-3-methyl-6-pyridin-4-yl-3H-pyrimidin-4-one,
6': (1S)-2-[5-(4-Chloro-benzoyl)-2,5-diaza-bicyclo[2.2.1]hept-2-yl]-3-methyl-6-pyridin-4-yl-3H-pyrimidin-4-one,
7': (1S)-2-(5-Benzyl-2,5-diaza-bicyclo[2.2.1]hept-2-yl)-3-methyl-6-pyridin-4-yl-3H-pyrimidin-4-one,
8': (1S)-2-[5-(4-Fluoro-benzoyl)-2,5-diaza-bicyclo[2.2.1]hept-2-yl]-3-methyl-6-pyridin-4-yl-3H-pyrimidin-4-one,
9': (1S)-2-[5-(4-Fluoro-phenyl)-2,5-diaza-bicyclo[2.2.1]hept-2-yl]-3-methyl-6-pyridin-4-yl-3H-pyrimidin-4-one,
10':(1S)-2-[5-(4-Methyl-benzoyl)-2,5-diaza-bicyclo[2.2.1]hept-2-yl]-3-methyl-6-pyridin-4-yl-3H-pyrimidin-4-one,
11':(1S)-2-[5-(3-Fluoro-phenyl)-2,5-diaza-bicyclo[2.2.1]hept-2-yl]-3-methyl-6-pyridin-4-yl-3H-pyrimidin-4-one,
12': 1S)-3-Methyl-6-pyridin-4-yl-2-(5-pyridin-3-yl-2,5-diaza-bicyclo[2.2.1]hept-2-yl)-3H-pyrimidin-4-one,
13':(1S)-2-[5-(3-Methoxy-benzoyl)-2,5-diaza-bicyclo[2.2.1]hept-2-yl]-3-methyl-6-pyridin-4-yl-3H-pyrimidin-4-one,
14': (1S)-2-[5-(3-Methyl-benzoyl)-2,5-diaza-bicyclo[2.2.1]hept-2-yl]-3-methyl-6-pyridin-4-yl-3H-pyrimidin-4-one,
15':(1S)-2-[5-(4-Ethoxy-benzoyl)-2,5-diaza-bicyclo[2.2.1]hept-2-yl]-3-methyl-6-pyridin-4-yl-3H-pyrimidin-4-one,
16': (1S)-2-[5-(4-Trifluoromethyl-benzoyl)-2,5-diaza-bicyclo[2.2.1]hept-2-yl]-3-m ethyl-6-pyridin-4-yl-3H-pyrimidin-4-one
17':(1S)-2-[5-(4-Phenyl-benzoyl)-2,5-diaza-bicyclo[2.2.1]hept-2-yl]-3-methyl-6-pyridin-4-yl-3H-pyrimidin-4-one, and
18':(1S)-2-[5-(3-Fluoro-benzoyl)-2,5-diaza-bicyclo[2.2.1]hept-2-yl]-3-methyl-6-pyridin-4-yl-3H-pyrimidin-4-one.

As a further object, the present invention concerns also methods for preparing the 2-(diaza-bicyclo-alkyl)-pyrimidone compounds represented by the aforementioned formula (I).

These compounds can be prepared, for example, according to methods explained below.

Preparation Method 2-(Diaza-bicyclo-alkyl)-pyrimidone compounds represented by the aforementioned formula (I), wherein R2 is as defined previously but not a hydrogen, may be prepared according to the method described in the scheme 1.

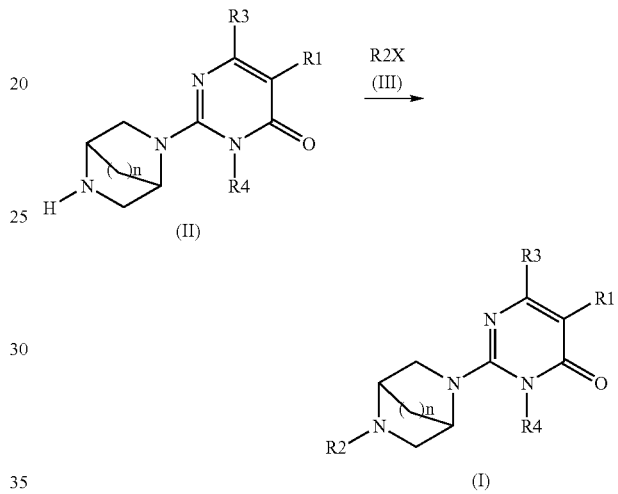

(In the above scheme the definition of R1, R3, R4 and n are the same as those already described for compound of formula (I)).

Following this method, the pyrimidinone derivative represented by the above formula (II), wherein R1, R3, R4 and n are as defined for compound of formula (1), is allowed to react, according to well known method in the art, with a compound of formula (III), wherein R2 is as defined for compound of formula (I) but not a hydrogen. For example the reaction may be carried out in a presence of a base such as alkoxide, amine or carbonate bases such as sodium tert-butoxide, triethylamine or cesium carbonate, in a solvent such as tetrahydrofuran or dimethylformamide and the like to give compound of formula (I).

More particularly, when R2 is an aryl group or a heteroaryl group such as defined for compound of formula (I), the reaction may be carried out according to Buchwald et al's method by a palladium-catalyzed amination (*J. Org. Chem.* 1997, 62, 6066–6068; *J. Am. Chem. Soc.* 1996, 118, 7217–7218). That is, the reaction is carried out in a presence of alkoxide, amine or carbonate bases, for example sodium tert-butoxide, triethylamine or cesium carbonate, and a palladium catalyst such as for example palladium(II) acetate with a ligand such as (R)-(+)-2,2'-bis(diphenylphosphino)-1,1'-binaphthyl, in a solvent such as tetrahydrofuran, dimethylformamide, tetraglyme or polyethylene glycol, at a suitable temperature ranging from 25° to 130° C. under inert atmosphere.

Alternatively, 2-(diaza-bicyclo-alkyl)-pyrimidone compounds represented by the aforementioned formula (I), wherein R2 is as defined previously for compound of formula (I), may be prepared according to scheme 2.

Scheme 2

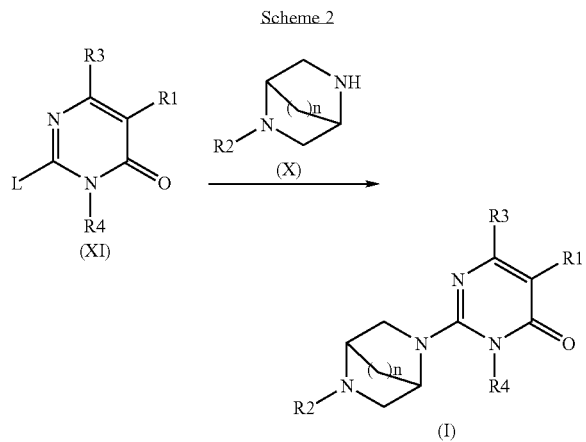

(In the above scheme the definition of R1, R2, R3, R4 and n are the same as already described for compound of formula (I)).

Following this method, compound of formula (XI), wherein R1, R3 and R4 are as defined for compound of formula (I) and L represents a leaving group such as for example a chlorine or bromine atom, is allowed to react with a compound of formula (X) wherein n and R2 are as defined for compound of formula (I). The reaction may be carried out in a presence of a base such as for example sodium hydride or triethylamine in a solvent such as dimethylformamide or tetrahydrofuran at a temperature ranging from 20° to 60° C.

The compound of formula (II) may be prepared according to the method defined in scheme 3.

Scheme 3

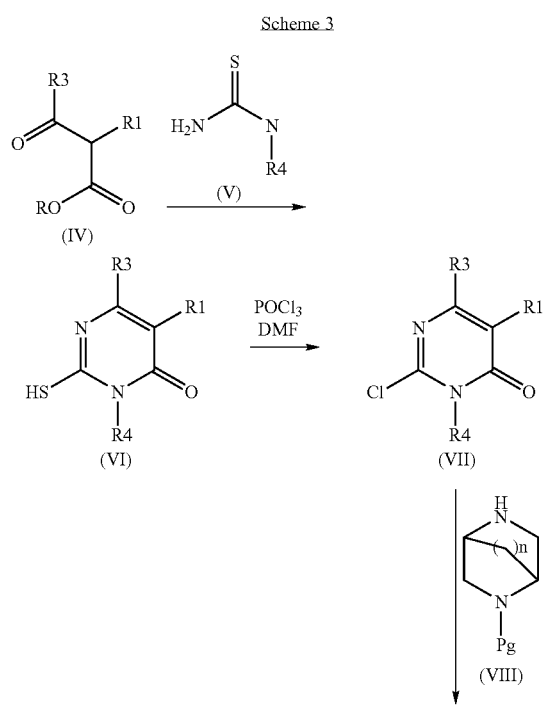

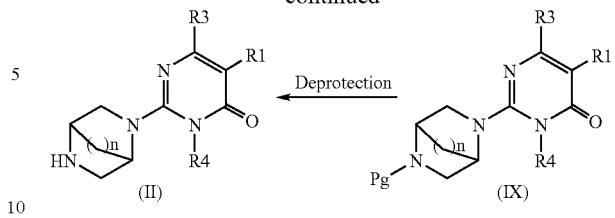

(In the above scheme the definition of R1, R3, R4 and n are the same as already described for compound of formula (I)).

According to this method, the 3-ketoester of formula (IV), wherein R1 and R3 are as defined for compound formula (I) and R is an alkyl group such as for example a methyl or ethyl group, is allowed to react with N-alkylthiourea of formula (V) wherein R4 is as defined for compound of formula (I). The reaction may be carried out in the presence of a base such as 1,8-diazabicyclo[5.4.0]undec-7-ene, in a alcoholic solvent such as ethanol, at a suitable temperature ranging from 25° to 140° C. under ordinary air to give the thiopyrimidone derivative of formula (VI). The thiopyrimidone derivative of formula (VI) is allowed to react with phosphorus oxychloride in a solvent such as dimethylformamide, at a suitable temperature ranging from 0° to 55° C. under argon atmosphere to give the 2-chloropyrimidone derivative of formula (VII). This latter of formula (VII) is then reacted with a compound of formula (VIII), wherein Pg is a protecting group such as for example a tert-butoxycarbonyl group, in the presence of a base such as triethylamine in a solvent such as tetrahydrofuran, at a suitable temperature ranging from 0° to 25° C., to give compound of formula (IX). The compound of formula (IX) is then deprotected according to well known method in the art such as for example when the protecting group is a tert-butoxycarbonyl group, in the presence of trifluoroacetic acid in a solvent such as dichloromethane at room temperature to give the aforementioned formula (II).

Alternatively, compounds of formula (II) wherein R1 represents a halogen atom such as a bromine atom or a chlorine atom, may be obtained by halogenation of a compound of formula (II) wherein R1 is a hydrogen atom. The reaction may be carried out in an acidic medium such as acetic acid or propionic acid, in presence of bromosuccinimide or chlorosuccinimide, or bromine.

In addition, compounds of formula (II), wherein R1 represents a fluorine atom, may be obtained by analogy to the method described in Tetrahedron Letters, Vol. 30,N° 45,pp 6113–6116, 1989.

Compounds of formula (III), (IV), (V), (VIII), (XI) and (X) are commercially available or may be synthesized according to well-known methods to one skilled in the art.

For example compounds of formula (IV), wherein R3 and R1 are as defined for compound of formula (I) and R is an alkyl group such as a methyl or an ethyl, can be prepared by reacting a pyrimidine-carboxylic acid or pyridine-carboxylic acid, optionally substituted by a $C_{1-4}$ alkyl group, $C_{1-4}$ alkoxy group or an halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20° to 70° C.

For example compounds of formula (VIII) with the absolute configuration (1R) can be prepared according to EP-400661.

As a further object, the present invention concerns also the compound of formula (II) as intermediate for preparing compounds of formula (I).

In the above reactions, protection or deprotection of a functional group may sometimes be necessary. A suitable protecting group Pg can be chosen depending on the type of the functional group, and a method described in the literature may be applied. Examples of protecting groups, of protection and deprotection methods are given for example in Protective groups in Organic Synthesis Greene et al., 2nd Ed. (John Wiley & Sons, Inc., New York).

The compounds of the present invention have inhibitory activity against GSK3β.

Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administration such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

The present invention will be explained more specifically with reference to the following general examples, however, the scope of the present invention is not limited to these examples.

Example 1

Compound N°7 of Table 1

(1S)-5-(1-Methyl-6-oxo-1,6-dihydro-[4,4']bipyrimidinyl-2-yl)-2,5-diaza-bicyclo[2.2.1]heptane-2-carboxylic acid tert-butyl ester. (Free base)

1.1. 2-Mercapto-1-methyl-1H-[4,4']bipyrimidinyl-6-one

A mixture containing 77.0 g (0.4 mol) of ethyl 3-(4-pyrimidinyl)-3-oxopropionate (prepared by analogy to the method described in patent DE 2705582), 107.0 g (1.19 mol) of N-methylthiourea, 60.4 g (0.4 mol) of 1,8-diazabicyclo[5.4.0]undec-7-ene in 773 ml of ethanol was heated under reflux during 2 h.

The cooled mixture was treated with 25.8 ml (0.40 mol) of methanesulfonic acid diluted in 157.2 ml of water and the precipitate recovered by filtration to afford 72 g of pure product as a yellow solid.

Mp: 219–221° C.

1.2 2-Chloro-1-methyl-1H-[4,4']bipyrimidinyl-6-one

To a solution of 300 ml of dimethylformamide was added 70 ml (0.75 mol) of phosphorus oxychloride at 0° C. and the resulting solution was stirred at same temperature for 15 min.

There is added 67.1 g (0.305 mol) of 2-mercapto-1-methyl-1H-[4,4']bipyrimidinyl-6-one and the resulting solution was stirred at 55° C. for 2 h.

The mixture was poured into ice-water, adjusted to pH 8 with sodium hydrogen carbonate and extracted with ethyl acetate. The organic extracts were dried over sodium sulfate and evaporated to give 44.6 g (66%) of the desired compound.

Mp: 150–152° C.

1.3 (1S)-5-(1-Methyl-6-oxo-1,6-dihydro-[4,4']bipyrimidinyl-2-yl)-2,5-diaza-bicyclo[2.2.1]heptane-2-carboxylic acid tert-butyl ester.

A mixture containing 1.95 ml (14 mmol) of triethylamine, 2.45 g (11 mmol) of 2-chloro-1-methyl-1H-[4,4']bipyrimidinyl-6-one, 2.58 g (13 mmol) of (1S)-2,5-diaza-bicyclo[2.2.1]heptane-2-carboxylic acid tert-butyl ester in 100 ml of anhydrous tetrahydrofuran was stirred at room temperature for 2 h. Water was added to the cooled mixture and the resulting solution extracted with ethyl acetate. The combined extracts were washed with saturated aqueous ammonium chloride and evaporated. The crude product was purified by chromatography on silica gel eluting with a mixture of dichloromethane/methanol in the proportions 100/0 to 98/2 to afford 4.2 g of pure product as a white solid.

Mp: 198–200° C.

RMN(200 MHz; DMSO-d$^6$): 9.25 (s, 1H); 8.97 (d, 1H); 8.19 (s, 1H); 6.81 (s, 1H); 4.85 (br s, 1H); 4.42 (br s, 1H); 3.84 (dd, 1H); 3.56–3.74 (m, 1H); 3.35–3.54 (m, 2H); 3.35 (s, 3H); 1.88 (br s, 2H); 1.34 (s, 9H).

Example 2

Compound N°14 of Table 1

(1S)-2-(2,5-Diaza-bicyclo[2.2.1]hept-2-yl)-1-methyl-1H-[4,4']bipyrimidinyl-6-one hydrochloride (1:1)

To a solution of 4.45 g (11.58 mmol) of (1S)-5-(1-methyl-6-oxo-1,6-dihydro-[4,4']bipyrimidinyl-2-yl)-2,5-diaza-bicyclo[2.2.1]heptane-2-carboxylic acid tert-butyl ester in 25 ml of anhydrous dichloromethane was added 10.71 ml (139 mmol) of trifluoroacetic acid and the resulting mixture was stirred at room temperature for 2 h.

The mixture was poured into ice-water, adjusted to pH 8 with potassium carbonate and extracted with chloroform. The organic extracts were dried over sodium sulfate and evaporated. The product obtained in the form of free base was transformed into the hydrochloride salt to give 4 g (69%) of pure compound as a yellow solid.

Mp: 275–277° C.

RMN (200 MHz; DMSO-d$^6$): 9.28 (s, 1H); 9.15 (br s, 1H(NH)); 8.96 (d, 1H) 8.22 (d, 1H); 6.88 (s, 1H); 4.88 (br s, 1H); 4.43 (br s, 1H); 3.89 (dd, 1H); 3.69 (br d, 1H); 3.24–3.46 (m, 2H); 3.33 (s, 3H); 2.03 (AB, 2H).

Example 3

Compound N°2 of Table 1

(1S)-1-Methyl-2-(5-pyridin-3-yl-2,5-diaza-bicyclo[2.2.1]hept-2-yl)-1H-[4,4']bipyrimidinyl-6-one hydrochloride (1:1)

A mixture containing 1.76 g (6.28 mmol) of (1S)-2-(2,5-diaza-bicyclo[2.2.1]hept-2-yl)-1-methyl-1H-[4,4']bipyrimidinyl-6-one, 2.18 ml (22.67 mmol) of 3-bromopyridine, 3.44 g (10.56 mmol) of cesium carbonate, 187 mg (0.3 mmol) of (R)-(+)-2,2'-bis(diphenylphosphino)-1,1'-binaphthyl and 67 mg (0.3 mmol) of palladium(II) acetate in 100 ml of anhydrous tetrahydrofuran under argon atmosphere was stirred under reflux for 18 h. The mixture was filtered and water was added to the mixture and the resulting solution extracted with chloroform. The combined extracts were washed with saturated aqueous ammonium chloride and evaporated. The crude product was purified by chromatography on silica gel eluting with a mixture of dichloromethane/methanol in the proportions 100/0 to 95/5. The product obtained in the form of free base was transformed into the hydrochloride salt to give 650 mg (26%) of pure compound as a solid.

Mp: 180–182° C. RMN (200 MHz; DMSO-d$^6$): 9.22 (d, 1H); 8.98 (d, 1H); 8.22 (dd, 1H); 8.13 (br s, 1H); 7.98 (t, 1H); 7.63–7.78 (m, 2H); 6.77 (s, 1H); 5.02 (s, 1H); 4.87 (s, 1H) 3.90 (d, 1H); 3.72 (s, 2H); 3.58 (d, 1H); 3.31 (s, 3H); 2.10 (AB, 2H).

Example 4

Compound N°16 of Table 1

(1S)-2-(5-Benzoyl-2,5-diaza-bicyclo[2.2.1]hept-2-yl)-1-methyl-1H-[4,4']bipyrimidinyl-6-one To a solution of 0.13 g (0.46 mmol) of (1S)-2-(2,5-diaza-bicyclo[2.2.1]hept-2-yl)-1-methyl-1H-[4,4']bipyrimidinyl- 6-one in 3 ml of anhydrous dimethylformamide was added 24 mg (0.6 mmol) of sodium hydride and the resulting mixture was stirred at 0° C. for 15 min.

There is added 0.07 ml (0.6 mmol) of benzoyl chloride and the resulting solution was stirred at 0° C. for 2 h.

Water was added to the mixture and the resulting solution extracted with ethyl acetate. The combined extracts were washed with saturated aqueous ammonium chloride and evaporated. The crude product was purified by chromatography on silica gel eluting with a mixture of dichloromethane/methanol in the proportions 100/0 to 97/3 to give 90 mg (50%) of pure compound as a solid.

Mp: 133–135° C.

RMN (400 MHz; DMSO-d$^6$): (Two conformers are present in the NMR spectra. Only the chemical displacements of the major one are given) 9.31 (s, 1H); 9.05 (d, 1H); 8.30 (d, 1H); 7.37–7.60 (m, 5H); 6.89 (s, 1H); 4.96 (s, 1H); 4.92 (s, 1H) 3.72–3.94 (m, 2H); 3.39 (s, 3H); 3.22–3.35 (m, 2H); 1.91–2.12 (m, 2H).

Example 5

Compound N°1' of Table 2

(1S)-5-(1-Methyl-6-oxo-4-pyridin-4-yl-1,6-dihydro-pyrimidin-2-yl)-2,5-diaza-bicyclo[2.2.1]heptane-2-carboxylic acid tert-butyl ester. (Free base)

5.1 2-Mercapto-3-methyl-6-pyridin-4-yl-3H-pyrimidin-4-one

A mixture containing 70.0 g (0.36 mol) of ethyl 3-(4-pyridinyl)-3-oxopropionate, 98.1 g (1.09 mol) of N-methylthiourea, 55.0 g (0.36 mol) of 1,8-diazabicyclo[5.4.0]undec-7-ene in 551 ml of ethanol is heated under reflux during 2 h.

The cooled mixture is treated with 34.9 ml (0.36 mol) of methanesulfonic acid in 143.6 ml of water and the precipitate recovered by filtration to afford 60.4 g of pure product as a white solid.

Mp: 250–252° C.

5.2 2-Chloro-3-methyl-6-pyridin-4-yl-3H-pyrimidin-4-one hydrochloride (1:1)

To a solution of 180 ml of dimethylformamide is added 16 ml (0.17 mol) of phosphorus oxychloride at 0° C. and the resulting solution is stirred at same temperature for 20 min.

There is added 24.15 g (0.11 mol) of 2-mercapto-3-methyl-6-pyridin-4-yl-3H-pyrimidin-4-one and the resulting solution is stirred at 70° C. for 5 h.

The mixture is poured into ice-water and the precipitate recovered by filtration to afford 28 g of pure product as a white solid.

Mp: 261–263° C.

5.3 (1S)-5-(1-Methyl-6-oxo-4-pyridin-4-yl-1,6-dihydro-pyrimidin-2-yl)-2,5-diaza-bicyclo[2.2.1]heptane-2-carboxylic acid tert-butyl ester. (Free base)

A mixture containing 10.7 ml (78.14 mmol) of triethylamine, 13.6 g (52.7 mmol) of 2-chloro-3-methyl-6-pyridin-4-yl-3H-pyrimidin-4-one hydrochloride (1:1), 6.0 g (30.24 mmol) of (1S)-2,5-diaza-bicyclo[2.2.1]heptane-2-carboxylic acid tert-butyl ester in 500 ml of anhydrous dimethylformamide is stirred at 20° C. for 6 h. Water is added to the cooled mixture and the resulting solution extracted with ethyl acetate. The combined extracts are washed with saturated aqueous ammonium chloride and saturated aqueous sodium chloride then-evaporated. The crude product is refluxed in diethylether for 1 h to afford 8.36 g of pure product as a brown solid.

Mp: 174–176° C.

RMN (200 MHz; CDCl$_3$): 8.73 (d, 2H); 7.78 (d, 2H); 6.58 (s, 1H); 4.83 (br s, 1H); 4.62 (br d, 1H); 3.69–4.02 (m, 1H); 3.77 (dd, 1H); 3.34–3.64 (m, 2H); 3.49 (s, 3H); 2.00 (br s, 2H); 1.49 (s, 9H).

Example 6

Compound N°2' of Table 2

(1S)-2-(2,5-Diaza-bicyclo[2.2.1]hept-2-yl)-3-methyl-6-pyridin-4-yl-3H-pyrimidin-4-one hydrochloride (1:2)

To a solution of 8.36 g (21.8 mmol) of (1S)-5-(1-methyl-6-oxo-4-pyridin-4-yl-1,6-dihydro-pyrimidin-2-yl)-2,5-diaza-bicyclo[2.2.1]heptane-2-carboxylic acid tert-butyl ester in 50 ml of anhydrous dichloromethane is added 20 ml (261.6 mmol) of trifluoroacetic acid and the resulting mixture is stirred at room temperature for 2 h. The mixture is poured into ice-water, adjusted to pH 8 with potassium carbonate and extracted with chloroform. The organic extracts were dried over sodium sulfate and evaporated. The crude product is triturated with ethyl acetate to afford 5 g of pure product as a brown solid which was transformed into the dihydrochloride salt.

Mp: 240–242° C.

RMN (200 MHz; DMSO-d 6): 9.18 (br s, 1H(NH)); 8.88 (d, 2H); 8.38 (d, 2H); 6.90 (s, 1H); 4.89 (br s, 1H); 4.43 (br s, 1H); 3.84 (AB, 2H); 3.55–3.78 (m, 2H); 3.38 (s, 3H); 2.03 (AB, 2H).

Example 7

Compound N° 12' of Table 2

(1S)-3-Methyl-6-pyridin-4-yl-2-(5-pyridin-3-yl-2,5-diaza-bicyclo[2.2.1]hept-2-yl)-3H-pyrimidin-4-one A mixture containing 0.2 g (0.71 mmol) of (1S)-2-(2,5-diaza-bicyclo[2.2.1]hept-2-yl)-3-methyl-6-pyridin-4-yl-3H-pyrimidin-4-one, 3.335 g (2.12 mmol) of 3-bromopyridine, 0.322 g (0.99 mmol) of cesium carbonate, 18 mg (0.028 mmol) of (+/−)-2,2'-bis(diphenylphosphino)-1,1'-binaphthyl and 6 mg (0.028 mmol) of palladium(II) acetate in 100 ml of anhydrous tetrahydrofuran under argon atmosphere is stirred under reflux for 18 h. The mixture is filtered. Water is added to the filtrate and the resulting solution extracted with chloroform. The combined extracts are washed with saturated aqueous ammonium chloride and evaporated. The crude product is purified by chromatography on silica gel eluting with a mixture of dichloromethane/methanol in the proportions 100/0 to 95/5 to give 119 mg of pure compound as a solid.

Mp: 179–181° C.

RMN (200 MHz; DMSO-d$^6$): 9.65 (d, 2H); 7.98 (s, 1H); 7.91 (d, 2H); 7.79 (d, 1H); 6.90–7.15 (m, 2H); 6.55 (s, 1H); 4.92 (br s, 1H); 4.69 (br s, 1H); 3.85 (dd, 1H); 3.67 (dd, 1H); 3.42–3.60 (m, 2H); 3.28 (s, 3H); 2.05 (br s, 2H).

Example 8

Compound N° 10' of Table 2

(1S)-2-[5-(4-Methyl-benzoyl)-2,5-diaza-bicyclo[2.2.1]hept-2-yl-]-3-methyl-6-pyridin-4-yl-3H-pyrimidin-4-one To a solution of 00.10 g (0.35 mmol) of (1S)-2-(2,5-diazabicyclo[2.2.1]hept-2-yl)-3-methyl-6-pyridin-4-yl-3H-pyrimidin-4-one in 3 ml of anhydrous tetrahydrofuran is added 0.06 ml (0.46 mmol) of anhydrous triethylamine and the resulting mixture is stirred at room temperature for 20 min.

To the cooled mixture is added 0.064 ml (0.46 mmol) of 4-methyl-benzoyl chloride and the resulting solution allowed to stir at room temperature for 2 h. Water is added to the mixture and the resulting solution extracted with dichloromethane. The combined extracts are washed with saturated aqueous ammonium chloride and evaporated. The crude product is purified by chromatography on silica gel eluting with a mixture of dichloromethane/methanol in the proportions 97/3 to give 106 mg of pure compound as a solid.

Mp: 118–120° C.

RMN (200 MHz; CDCl$_3$): 8.72 (br s, 2H); 7.75 (br d, 2H); 7.45 (br s, 2H) 7.15–7.35 (m, 2H); 6.58 (br s, 1H); 4.90 (AB, 2H); 3.65–4.26 (m, 4H); 3.50 (s, 3H); 2.41 (br s, 3H); 2.09 (br d, 2H).

A list of chemical structures and physical data for compounds of the aforementioned formula (I) illustrating the present invention is given in table 1. The compounds have been prepared according to the methods of the example.

In the table 1 and 2, (S) or (R) indicate the stereochemistry of the carbon atom, Ph represents a phenyl group.

In table 1 R3 is an unsubstituted 4-pyrimidine ring and R4 is a methyl group.

In table 2 R3 is an unsubstituted 4-pyridine ring and R4 is a methyl group.

TABLE 1

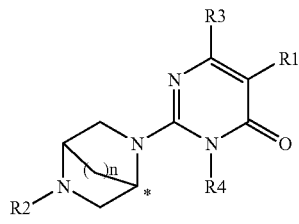

(I)

| N° | Absolute configuration* | R1 | R2 | n | Mp ° C. | salt |
|---|---|---|---|---|---|---|
| 1 | (1S) | H | Ph-pyridin-3-yl (5-phenyl-pyridin-3-yl-methyl) | 1 | 52 | (1:1) (hydrochloride) |
| 2 | (1S) | H | pyridin-3-yl-methyl | 1 | 180–182 | (1:1) (hydrochloride) |
| 3 | (1S) | H | quinolin-3-yl-methyl | 1 | 183–184 | (1:1) (hydrochloride) |
| 4 | (1R) | H | pyridin-3-yl-methyl | 1 | 178–180 | (1:1) (hydrochloride) |
| 5 | (1S) | H | 4-fluorophenyl-methyl | 1 | 202–204 | Free base |
| 6 | (1S) | H | 6-chloroquinolin-3-yl-methyl | 1 | 232–234 | Free base |

TABLE 1-continued
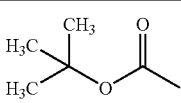
(I)
| N° | Absolute configuration* | R1 | R2 | n | Mp ° C. | salt |
|---|---|---|---|---|---|---|
| 7 | (1S) | H | 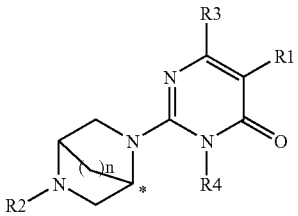 | 1 | 198–200 | Free base |
| 8 | (1S) | H | 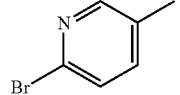 | 1 | 245–247 | Free base |
| 9 | (1S) | H | 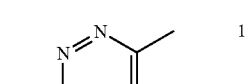 | 1 | 265–267 | Free base |
| 10 | (1S) | H | 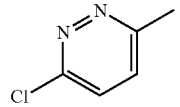 | 1 | 241–243 | Free base |
| 11 | (1S) | H | 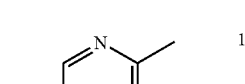 | 1 | 217–219 | Free base |
| 12 | (1S) | H | 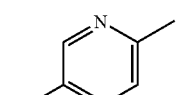 | 1 | 237–239 | Free base |
| 13 | (1S) | H | 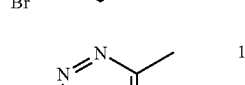 | 1 | 203–205 | Free base |
| 14 | (1S) | H | H | 1 | 275–277 | (1:1) (hydrochloride) |
| 15 | (1S) | H | 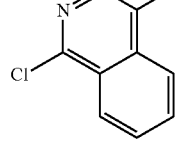 | 1 | 225–227 | Free base |
| 16 | (1S) | H | 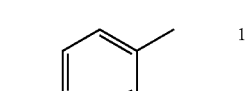 | 1 | 133–135 | Free base |

TABLE 1-continued (I)

| N° | Absolute configuration* | R1 | R2 | n | Mp ° C. | salt |
|---|---|---|---|---|---|---|
| 17 | (1S) | H | 4-methylsulfonylphenyl (H₃C-C₆H₄-SO₂-) | 1 | 212–214 | Free base |
| 18 | (1S) | H | benzyl acetate (PhCH₂-O-C(O)-CH₂-) | 1 | 100–102 | Free base |
| 19 | (1S) | H | phenethyl (Ph-CH₂-CH₂-) | 1 | 110–112 | Free base |
| 20 | (1S) | H | benzyl-CH₂- (Ph-CH₂-CH₂-) | 1 | 155–157 | Free base |
| 21 | (1S) | H | (1-hydroxy-1-phenyl)propyl | 1 | 187–189 | Free base |
| 22 | (1S) | H | (pyridin-2-yl)methyl | 1 | 280–282 | (1:1) (hydrochloride) |
| 23 | (1S) | H | (pyridin-4-yl)methyl | 1 | 252–254 | (1:1) (hydrochloride) |
| 24 | (1S) | H | (4-bromophenyl)carbonylmethyl | 1 | 142–144 | Free base |
| 25 | (1S) | H | (4-chlorophenyl)carbonylmethyl | 1 | 152–154 | Free base |

TABLE 1-continued
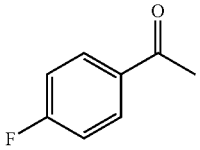
| N° | Absolute configuration* | R1 | R2 | n | Mp ° C. | salt |
|---|---|---|---|---|---|---|
| 26 | (1S) | H | 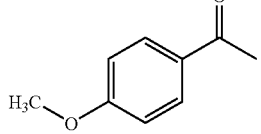 | 1 | 191–193 | Free base |
| 27 | (1S) | H | 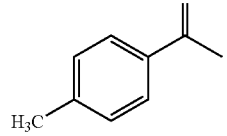 | 1 | 131–133 | Free base |
| 28 | (1S) | H | 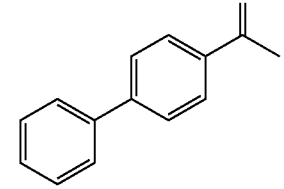 | 1 | 144–147 | Free base |
| 29 | (1S) | H | 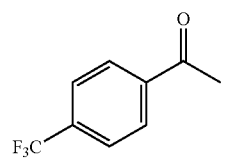 | 1 | 135–137 | Free base |
| 30 | (1S) | H | 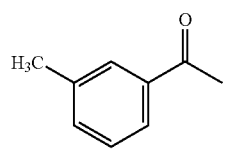 | 1 | 207–209 | Free base |
| 31 | (1S) | H | 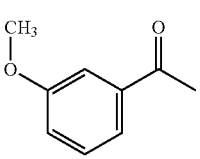 | 1 | 181–183 | Free base |
| 32 | (1S) | H |  | 1 | 185–187 | Free base |

TABLE 1-continued
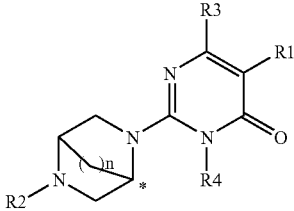
(I)
| N° | Absolute configuration* | R1 | R2 | n | Mp ° C. | salt |
|----|-------------------------|----|----|---|---------|------|
| 33 | (1S) | H | 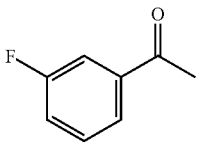 | 1 | 178–108 | Free base |
| 34 | (1S) | H | 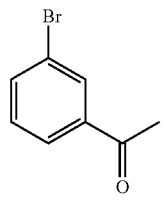 | 1 | 199–201 | Free base |
| 35 | (1S) | H | 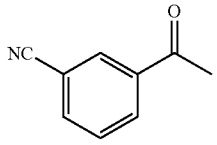 | 1 | 228–230 | Free base |
| 36 | (1S) | H | 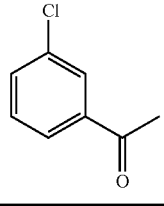 | 1 | 192–194 | Free base |
TABLE 2
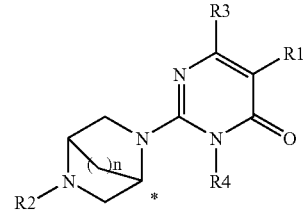
(I)
| N° | Absolute configuration | R1 | R2 | n | Mp ° C. | salt |
|----|------------------------|----|----|---|---------|------|
| 1' | 1 (S) | H | 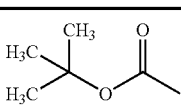 | 1 | 174–176 | Free base |
| 2' | 1-(S) | H | H | 1 | 240–242 | (1:2) (hydrochloride) |

TABLE 2-continued
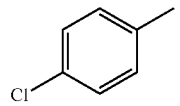
(I)
| N° | Absolute configuration | R1 | R2 | n | Mp ° C. | salt |
|---|---|---|---|---|---|---|
| 3' | 1-(S) | H | 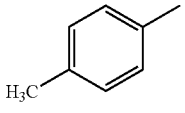 | 1 | 251–253 | Free base |
| 4' | 1-(S) | H | 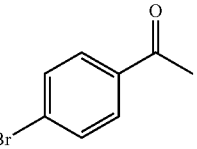 | 1 | 123–125 | Free base |
| 5' | 1-(S) | H | 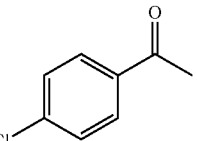 | 1 | 115–117 | (1:1) (hydrochloride) |
| 6' | 1-(S) | H | 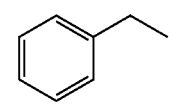 | 1 | 116–118 | (1:1) (hydrochloride) |
| 7' | 1-(S) | H | 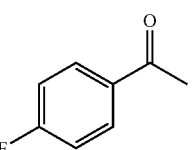 | 1 | 162–164 | Free base |
| 8' | 1-(S) | H | 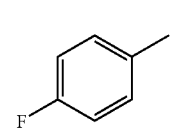 | 1 | 118–120 | Free base |
| 9' | 1-(S) | H | 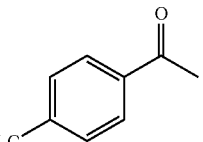 | 1 | 185–187 | Free base |
| 10' | 1-(S) | H | 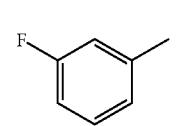 | 1 | 118–120 | Free base |
| 11' | 1-(S) | H |  | 1 | 184–186 | (1:1) (hydrobromide) |

TABLE 2-continued
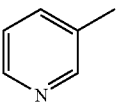
(I)
| N° | Absolute configuration | R1 | R2 | n | Mp ° C. | salt |
|---|---|---|---|---|---|---|
| 12' | 1-(S) | H | 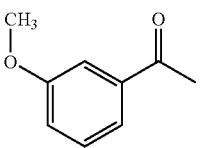 | 1 | 179–181 | Free base |
| 13' | 1-(S) | H | 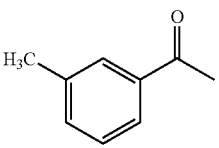 | 1 | 165–167 | Free base |
| 14' | 1-(S) | H | 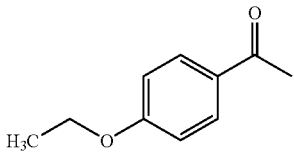 | 1 | 150–152 | Free base |
| 15' | 1-(S) | H | 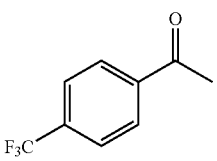 | 1 | 110–112 | Free base |
| 16' | 1-(S) | H | 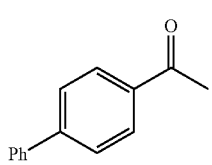 | 1 | 193–195 | Free base |
| 17' | 1-(S) | H | 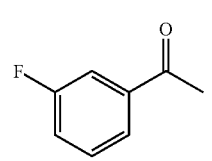 | 1 | 232–234 | Free base |
| 18' | 1-(S) | H |  | 1 | 155–157 | Free base |

Test Example

Inhibitory Activity of the Medicament of the Present Invention Against GSK3β

Two different protocols can be used.

In a first protocol: 7.5 μM of prephosphorylated GS1 peptide and 10 μM ATP (containing 300,000 cpm of $^{33}$P-ATP) were incubated in 25 mM Tris-HCl, pH 7.5, 0.6 mM DTT, 6 mM $MgCl_2$, 0.6 mM EGTA, 0.05 mg/ml BSA buffer for 1 hour at room temperature in the presence of GSK3beta (total reaction volume: 100 microliters).

In a second protocol: 4.1 μM of prephosphorylated GS 1 peptide and 42 μM ATP (containing 260,000 cpm $^{33}$P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3beta. Inhibitors were solubilised in DMSO (final solvent concentration in the reaction medium, 1%).

The reaction was stopped with 100 microliters of a solution made of 25 g polyphosphoric acid (85% $P_2O_5$), 126 ml 85% $H_3PO_4$, $H_2O$ to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry.

The phosphorylated GS-1 peptide had the following sequence:
NH2-YRRAAVPPSPSLSRHSSPHQS(P)EDEE-COOH.

The GSK3β inhibitory activity of the compounds of the present invention are expressed in $IC_{50}$, and as an illustration the range of $IC_{50}$'s of the compounds in table 1 is between 1 nanomolar to 1 micromolar concentrations.

For example compound No.24 of table 1 shows an $IC_{50}$ of 0.006 μM and compound No. 4' of table 2 shows an $IC_{50}$ of 0.004 μM.

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

INDUSTRIAL APPLICABILITY

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

What is claimed is:
1. A compound of formula (I)

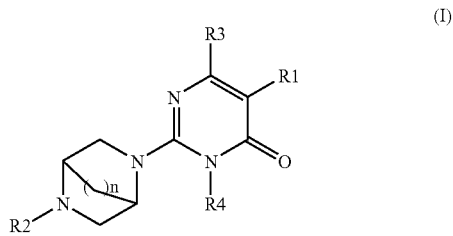

wherein:
R1 represents a hydrogen atom, a $C_{1-6}$ alkyl group or a halogen atom;
R2 represents a hydrogen atom, a $C_{1-6}$ alkyl group optionally substituted by 1 to 4 substituents selected from a halogen atom, a hydroxyl group, a $C_{1-4}$ alkoxy group; a $C_{1-2}$ perhalogenated alkyl group, a benzyl group, a phenethyl group, a benzyloxycarbonyl group, a $C_{1-4}$ alkoxy carbonyl group, a benzene ring, a naphthalene ring, a quinoline ring, a phthalazine ring, a 5,6,7,8-tetrahydronaphthalene ring, a pyridine ring, an indole ring, a pyrrole ring, a thiophene ring, a benzenesulfonyl group, a benzoyl group, a pyridazine ring, a furan ring and an imidazole ring; each of the benzyl group, the phenethyl group, the benzyloxycarbonyl group, the benzenesulfonyl group, the benzoyl group and the benzene, naphthalene, quinoline, phthalazine, 5,6,7,8-tetrahydronaphthalene, pyridine, indole, pyrrole and thiophene rings being optionally substituted by 1 to 4 substituents selected from a $C_{1-6}$ alkyl group, a benzene ring, a halogen atom, a $C_{1-2}$ perhalogenated alkyl group, a $C_{1-3}$ halogenated alkyl group, a hydroxyl group, a $C_{1-4}$ alkoxy group, a nitro group, a cyano group, an amino group, a $C_{1-6}$ monoalkylamino group and a $C_{2-10}$ dialkylamino group;
R3 represents a 2, 4 or 5-pyrimidine ring or a 2, 3 or 4-pyridine ring, the rings being optionally substituted by a $C_{1-4}$ alkyl group, $C_{1-4}$ alkoxy group or a halogen atom;
R4 represents a $C_{1-4}$ alkyl group optionally substituted by a hydroxyl group, a $C_{1-4}$ alkoxy group or a halogen atom and
n represents 1 or 2,
or a salt thereof.

2. The compound according to claim 1, wherein R3 represents an unsubstituted 4-pyrimidine ring or an unsubstituted 4-pyridine ring.

3. The compound according to claim 1, wherein, when R3 represents an optionally substituted pyrimidine ring, R2 represents a hydrogen atom; or an optionally substituted, by 1 to 4 substituents, benzyl group, phenethyl group, benzyloxycarbonyl group, $C_{1-4}$ alkoxy carbonyl group, benzene ring, quinoline ring, phthalazine ring, pyridine ring, benzenesulfonyl group, benzoyl group or pyridazine ring; provided that, when R3 represents an optionally substituted pyridine ring, R2 represents an optionally substituted pyridine ring, benzene ring, naphthalene ring, benzyl group, or benzoyl group.

4. The compound according to claim 1, which is selected from the group consisting of:
- (1S)-1-Methyl-2-[5-(5-phenyl-pyridin-3-yl)-2,5-diaza-bicyclo[2.2.1]hept-2-yl]-1H-[4,4']bipyrimidinyl-6-one,
- (1S)-1-Methyl-2-(5-pyridin-3-yl-2,5-diaza-bicyclo[2.2.1]hept-2-yl)-1H-[4,4']bipyrimidinyl-6-one,
- (1S)-1-Methyl-2-(5-quinolin-3-yl-2,5-diaza-bicyclo[2.2.1]hept-2-yl)-1H-[4,4']bipyrimidinyl-6-one,
- (1R)-1-Methyl-2-(5-pyridin-3-yl-2,5-diaza-bicyclo[2.2.1]hept-2-yl)-1H-[4,4']bipyrimidinyl-6-one,
- (1S)-2-[5-(4-Fluoro-phenyl)-2,5-diaza-bicyclo[2.2.1]hept-2-yl]-1-methyl-1H-[4,4']bipyrimidinyl-6-one,
- (1R)-2-[5-(6-Chloro-quinolin-3-yl)-2,5-diaza-bicyclo[2.2.1]hept-2-yl]-1-methyl-1H-[4,4']bipyrimidinyl-6-one,
- (1S)-5-(1-Methyl-6-oxo-1,6-dihydro-[4,4']bipyrimidinyl-2-yl)-2,5-diaza-bicyclo[2.2.1]heptane-2-carboxylic acid tert-butyl ester
- (1S)-2-[5-(6-Bromo-pyridin-3-yl)-2,5-diaza-bicyclo[2.2.1]hept-2-yl]-1-methyl-1H-[4,4']bipyrimidinyl-6-one,
- (1S)-2-[5-(6-Chloro-pyridazin-3-yl)-2,5-diaza-bicyclo[2.2.1]hept-2-yl]-1-methyl-1H-[4,4']bipyrimidinyl-6-one,
- (1S)-2-[5-(5-Bromo-pyridin-2-yl)-2,5-diaza-bicyclo[2.2.1]hept-2-yl]-1-methyl-1H-[4,4']bipyrimidinyl-6-one,
- (1S)-2-[5-(4-Chloro-phthalazin-1-yl)-2,5-diaza-bicyclo[2.2.1]hept-2-yl]-1-methyl-1H-[4,4']bipyrimidinyl-6-one,
- (1S)-2-[5-(4-Chloro-phenyl)-2,5-diaza-bicyclo[2.2.1]hept-2-yl]-1-methyl-1H-[4,4']bipyrimidinyl-6-one,
- (1S)-2-[5-(3-Fluoro-phenyl)-2,5-diaza-bicyclo[2.2.1]hept-2-yl]-1-methyl-1H-[4,4']bipyrimidinyl-6-one,
- (1S)-2-(2,5-Diaza-bicyclo[2.2.1]hept-2-yl)-1-methyl-1H-[4,4']bipyrimidinyl-6-one,
- (1S)-1-Methyl-2-(5-p-tolyl-2,5-diaza-bicyclo[2.2.1]hept-2-yl)-1H-[4,4']bipyrimidinyl-6-one,
- (1S)-2-(5-Benzoyl-2,5-diaza-bicyclo[2.2.1]hept-2-yl)-1-methyl-1H-[4,4']bipyrimidinyl-6-one,
- (1S)-1-Methyl-2-[5-(toluene-4-sulfonyl)-2,5-diaza-bicyclo[2.2.1]hept-2-yl]-1H-[4,4']bipyrimidinyl-6-one,
- (1S)-5-(1-Methyl-6-oxo-1,6-dihydro-[4,4']bipyrimidinyl-2-yl)-2,5-diaza-bicyclo[2.2.1]heptane-2-carboxylic acid benzyl ester
- (1S)-1-Methyl-2-(5-phenethyl-2,5-diaza-bicyclo[2.2.1]hept-2-yl)-1H-[4,4']bipyrimidinyl-6-one,
- (1S)-2-(5-Benzyl-2,5-diaza-bicyclo[2.2.1]hept-2-yl)-1-methyl-1H-[4,4']bipyrimidinyl-6-one,
- (1S)-2-[5-(2(S)-Hydroxy-2-phenyl-ethyl)-2,5-diaza-bicyclo[2.2.1]hept-2-yl]-1-methyl-1H-[4,4']bipyrimidinyl-6-one,
- (1S)-1-Methyl-2-(5-pyridin-2-yl-2,5-diaza-bicyclo[2.2.1]hept-2-yl)-1H-[4,4']bipyrimidinyl-6-one,
- (1S)-1-Methyl-2-(5-pyridin-4-yl-2,5-diaza-bicyclo[2.2.1]hept-2-yl)-1H-[4,4']bipyrimidinyl-6-one,
- (1S)-2-(5-(4-Bromo-benzoyl)-2,5-diaza-bicyclo[2.2.1]hept-2-yl)-1-methyl-1H-[4,4']bipyrimidinyl-6-one,
- (1S)-2-(5-(4-Chloro-benzoyl)-2,5-diaza-bicyclo[2.2.1]hept-2-yl)-1-methyl-1H-[4,4']bipyrimidinyl-6-one,
- (1S)-2-(5-(4-Fluoro-benzoyl)-2,5-diaza-bicyclo[2.2.1]hept-2-yl)-1-methyl-1H-[4,4']bipyrimidinyl-6-one,
- (1S)-2-(5-(4-Methoxy-benzoyl)-2,5-diaza-bicyclo[2.2.1]hept-2-yl)-1-methyl-1H-[4,4']bipyrimidinyl-6-one,
- (1S)-2-(5-(4-Methyl-benzoyl)-2,5-diaza-bicyclo[2.2.1]hept-2-yl)-1-methyl-1H-[4,4']bipyrimidinyl-6-one,
- (1S)-2-(5-(4-Phenyl-benzoyl)-2,5-diaza-bicyclo[2.2.1]hept-2-yl)-1-methyl-1H-[4,4']bipyrimidinyl-6-one,
- (1S)-2-(5-(4-Trifluoromethyl-benzoyl)-2,5-diaza-bicyclo[2.2.1]hept-2-yl)-1-methyl-1H-[4,4']bipyrimidinyl-6-one,
- (1S)-2-(5-(3-Methyl-benzoyl)-2,5-diaza-bicyclo[2.2.1]hept-2-yl)-1-methyl-1H-[4,4']bipyrimidinyl-6-one,
- (1S)-2-(5-(3-Methoxy-benzoyl)-2,5-diaza-bicyclo[2.2.1]hept-2-yl)-1-methyl-1H-[4,4']bipyrimidinyl-6-one,
- (1S)-2-(5-(3-Fluoro-benzoyl)-2,5-diaza-bicyclo[2.2.1]hept-2-yl)-1-methyl-1H-[4,4']bipyrimidinyl-6-one,
- (1S)-2-(5-(3-Bromo-benzoyl)-2,5-diaza-bicyclo[2.2.1]hept-2-yl)-1-methyl-1H-[4,4']bipyrimidinyl-6-one,
- (1S)-2-(5-(3-Cyano-benzoyl)-2,5-diaza-bicyclo[2.2.1]hept-2-yl)-1-methyl-1H-[4,4']bipyrimidinyl-6-one,
- (1S)-2-(5-(3-Chloro-benzoyl)-2,5-diaza-bicyclo[2.2.1]hept-2-yl)-1-methyl-1H-[4,4']bipyrimidinyl-6-one,
- (1S)-5-(1-Methyl-6-oxo-4-pyridin-4-yl-1,6-dihydro-pyrimidin-2-yl)-2,5-diaza-bicyclo[2.2.1]heptane-2-carboxylic acid tert-butyl ester
- (1S)-2-(2,5-Diaza-bicyclo[2.2.1]hept-2-yl)-3-methyl-6-pyridin-4-yl-3H-pyrimidin-4-one,
- (1S)-2-[5-(4-Chloro-phenyl)-2,5-diaza-bicyclo[2.2.1]hept-2-yl]-3-methyl-6-pyridin-4-yl-3H-pyrimidin-4-one,
- (1S)-3-Methyl-6-pyridin-4-yl-2-(5-p-tolyl-2,5-diaza-bicyclo[2.2.1]hept-2-yl)-3H-pyrimidin-4-one,
- (1S)-2-[5-(4-Bromo-benzoyl)-2,5-diaza-bicyclo[2.2.1]hept-2-yl]-3-methyl-6-pyridin-4-yl-3H-pyrimidin-4-one,
- (1S)-2-[5-(4-Chloro-benzoyl)-2,5-diaza-bicyclo[2.2.1]hept-2-yl]-3-methyl-6-pyridin-4-yl-3H-pyrimidin-4-one,
- (1S)-2-(5-Benzyl-2,5-diaza-bicyclo[2.2.1]hept-2-yl)-3-methyl-6-pyridin-4-yl-3H-pyrimidin-4-one,
- (1S)-2-[5-(4-Fluoro-benzoyl)-2,5-diaza-bicyclo[2.2.1]hept-2-yl]-3-methyl-6-pyridin-4-yl-3H-pyrimidin-4-one,
- (1S)-2-[5-(4-Fluoro-phenyl)-2,5-diaza-bicyclo[2.2.1]hept-2-yl]-3-methyl-6-pyridin-4-yl-3H-pyrimidin-4-one,
- (1S)-2-[5-(4-Methyl-benzoyl)-2,5-diaza-bicyclo[2.2.1]hept-2-yl]-3-methyl-6-pyridin-4-yl-3H-pyrimidin-4-one,
- (1S)-2-[5-(3-Fluoro-phenyl)-2,5-diaza-bicyclo[2.2.1]hept-2-yl]-3-methyl-6-pyridin-4-yl-3H-pyrimidin-4-one,
- (1S)-3-Methyl-6-pyridin-4-yl-2-(5-pyridin-3-yl-2,5-diaza-bicyclo[2.2.1]hept-2-yl)-3H-pyrimidin-4-one,
- (1S)-2-[5-(3-Methoxy-benzoyl)-2,5-diaza-bicyclo[2.2.1]hept-2-yl]-3-methyl-6-pyridin-4-yl-3H-pyrimidin-4-one, (1S)-2-[5-(3-Methyl-benzoyl)-2,5-diaza-bicyclo[2.2.1]
hept-2-yl]-3-methyl-6-pyridin-4-yl-3H-pyrimidin-4-
one, (1S)-2-[5-(4-Ethoxy-benzoyl)-2,5-diaza-bicyclo[2.2.1]
hept-2-yl]-3-methyl-6-pyridin-4-yl-3H-pyrimidin-4-
one, (1S)-2-[5-(4-Trifluoromethyl-benzoyl)-2,5-diaza-bicyclo
[2.2.1]hept-2-yl]-3-methyl-6-pyridin-4-yl-3H-pyrimi-
din-4-one (1S)-2-[5-(4-Phenyl-benzoyl)-2,5-diaza-bicyclo[2.2.1]
hept-2-yl]-3-methyl-6-pyridin-4-yl-3H-pyrimidin-4-
one, and 1S)-2-[5-(3-Fluoro-benzoyl)-2,5-diaza-bicyclo[2.2.1]
hept-2-yl]-3-methyl-6-pyridin-4-yl-3H-pyrimidin-4-
one;

or a salt thereof.

5. A compound of formula (II)

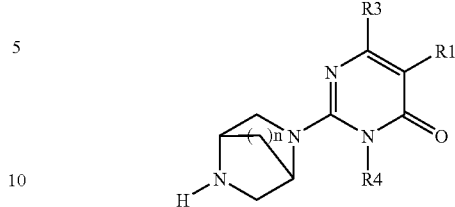

wherein R1, R3, R4 and n are as defined for compound of formula (I) according to claim 1.

6. A medicament comprising a pharmaceutically acceptable carrier and, as an active ingredient, a compound of claim 1 or a salt thereof.

7. The medicament of claim 6, wherein said active ingredient is a GSK3β inhibitor.

* * * * *